United States Patent [19]

Buerkley et al.

[11] 4,232,083

[45] Nov. 4, 1980

[54] IMAGING COMPOSITIONS AND METHODS

[75] Inventors: Donald D. Buerkley, Woodbury; Norman P. Sweeny, North Oaks; Daniel N. Vivona, Lake Elmo, all of Minn.

[73] Assignee: Minnesota Mining and Manufacturing Company, St. Paul, Minn.

[21] Appl. No.: 597,998

[22] Filed: Jul. 22, 1975

[51] Int. Cl.$^2$ ............................................. B32B 3/16
[52] U.S. Cl. ........................... 428/307; 260/500.5 H; 260/539; 260/558 R; 260/583 DD; 260/590 D; 260/619 B; 260/DIG. 4; 427/1; 427/145; 427/150; 427/151; 427/152; 428/488; 428/537; 428/914; 568/336
[58] Field of Search ................. 427/145, 1, 150–152; 428/411–307, 537, 488; 282/27.5; 260/DIG. 4, 619 B, 590 D, 558 R, 583 DD, 539 R, 500.5 H; 96/107

[56] References Cited

U.S. PATENT DOCUMENTS

| | | | |
|---|---|---|---|
| 1,509,872 | 9/1924 | Murray | 427/337 |
| 2,082,735 | 6/1937 | Heinecke | 427/1 |
| 2,104,586 | 1/1938 | Freudenheim | 427/1 |
| 2,235,632 | 3/1941 | Heinecke | 427/1 |
| 2,279,560 | 4/1942 | Dietrich | 260/500.5 H |
| 2,279,973 | 4/1942 | Dietrich | 260/500.5 H |
| 2,333,548 | 11/1943 | Niederl | 260/619 B |
| 2,346,665 | 4/1944 | Cupery | 260/500.5 H |
| 2,445,586 | 7/1948 | Simons | 427/1 |
| 3,098,099 | 7/1963 | Conte et al. | 260/590 D |
| 3,111,423 | 11/1963 | Ostlie | 428/537 |
| 3,345,344 | 10/1967 | Fetscher | 260/500.5 H |
| 3,432,327 | 3/1969 | Kan et al. | 427/150 |
| 3,507,900 | 4/1970 | Burk et al. | 260/500.5 H |
| 3,780,105 | 12/1973 | Idelson | 260/590 D |
| 3,823,022 | 7/1974 | Thomas | 427/151 |
| 3,912,831 | 10/1975 | Kan et al. | 427/150 |
| 3,920,863 | 11/1975 | Fraik | 427/150 |
| 3,937,864 | 2/1976 | Kohmura et al. | 427/150 |
| 3,996,397 | 12/1976 | Laridon et al. | 427/145 |

FOREIGN PATENT DOCUMENTS

| | | | |
|---|---|---|---|
| 535267 | 1/1957 | Canada | 427/150 |
| 866076 | 4/1961 | United Kingdom | 427/150 |
| 1042596 | 9/1966 | United Kingdom | 427/150 |
| 1042599 | 9/1966 | United Kingdom | 427/150 |

*Primary Examiner*—Ronald H. Smith
*Assistant Examiner*—Janyce A. Bell
*Attorney, Agent, or Firm*—Cruzan Alexander; Donald M. Sell; Warren R. Bovee

[57] ABSTRACT

Color-forming precursor compositions comprising a metal-complexing compound having a plurality of ligand groups and color-activating compositions comprising transition metal salts of oleophilic, organic acids are combined to form dark, permanent images on substrates. The methods and compositions are particularly useful for providing permanent fingerprints and other dermographs.

28 Claims, No Drawings

IMAGING COMPOSITIONS AND METHODS

The present invention relates to methods and compositions for providing dark, permanent images on paper and other substrates without employing conventional inks. More particularly, this invention provides means for providing permanent fingerprints on plain paper substrates which have not been printed or coated during manufacture or laminated to provide a color-capable surface. The components used in the imaging compositions of this invention will not soil or stain the subject's skin.

Two-component imaging systems wherein the components are combined to form a visibly colored area or image on paper or other substrates are known. See, for example, U.S. Pat. No. 3,682,673 and British Pat. No. 428,386. These systems are particularly advantageous in that the individual components are generally not themselves colored, but provide visible color on a substrate when the components are combined. Thus, if a transfer means is employed, such as a finger for making fingerprints, to contact and thereafter transfer one of the components to a sheet containing the other component, the transfer means, e.g. the finger, does not become soiled or stained since the components do not form a colored product until they react on the sheet.

The non-soiling feature of these systems is particularly desirable when personal records such as fingerprints or other dermographs are to be recorded on personal checks and the like at retail stores or other places of business. Conventional black fingerprinting inks are unacceptable under these conditions. However, when precise permanent images are required, the color-forming systems known in the prior art may not be satisfactory since the images tend to bleed, i.e. become blurred, shortly after formation due to the migration of the imaging material away from the reaction site. This migration phenomenon is caused by the presence of the oily, liquid cosolvents which must be present during the color-forming reaction. One means of preventing image degradation is to coat or print one of the color-forming components on a substrate, such as paper, using pigments in the coating which tend to absorb the liquid components and immobilize the image after formation. This method requires pretreatment of the paper sheet at the point of manufacture and may cause an undesirable stiffening or thickening of the paper substrate.

Another method of applying images to plain paper substrates is to employ an adhesive, sensitized label which has been coated with a color-forming component to provide a color-capable surface. This label can be applied to the paper sheet, such as the back of a personal check. After contacting a color-forming component carried in an absorbent pad, or the like, the subject's finger is pressed on the label and a print forms on the label.

Both of the aforementioned techniques, i.e., use of precoated substrates and sensitized labels, are unsatisfactory for use with personal checks since they require an expensive manufacturing step to pre-coat the check or the label and provide a stiffened and thickened sheet which cannot be satisfactorily processed by conventional counting, sorting and reading machines employed in the banking industry.

Accordingly, the need has arisen for an imaging system which can be conveniently used in public business establishments, which will not stain or soil the user's clothing or skin, which provides a substantially "zero thickness" image area on the substrate and which can employ unmodified substrates, that is, substrates which have not been manufactured, pre-treated or laminated to be made color-capable.

The present invention has overcome the problems associated with the prior art by providing methods and compositions for forming dark, intensely colored permanent images on plain paper or other receptive substrates. More particularly, the invention relates to two-component compositions which can be used to form dark, permanent dermographic images on plain paper substrates without soiling or staining the user's clothing or skin and which provide essentially a zero thickness image area.

The foregoing advantages are accomplished in the present invention by providing two-component, color-forming compositions wherein one of the components is a color-forming precursor composition comprising an organic, color-forming metal-complexing compound having a plurality of ligand groups. The complexing compound is capable of complexing with transition metal ions to form metal-containing products which are substantially insoluble in organic cosolvents for the compound. The complementary color-activating composition comprises the transition metal salt of an oleophilic, organic acid. At least one of the color-forming compositions preferably contains a cosolvent, i.e. a solvent which is a solvent for both the metal-complexing compound and the transition metal salt, included therewith.

Throughout this specification, the "color-forming precursor" composition is described as containing the metal-complexing compound and as being applied to a substrate from a transfer sheet or the like, while the "color-activating" composition is described as containing the transition metal salt and as being contained in an absorbent pad and the like. These terms and description are for convenience only, it being understood that either composition could be designated as the "precursor" and the other the "activator", and both can be carried, stored, and applied by similar means.

The color-forming precursor composition and the color-activating composition are separately prepared and are relatively colorless as separate compositions. When the two compositions are brought together, preferably in the presence of a cosolvent for both compositions, the metal-complexing compound and the transition metal form intensely colored inner complex compounds substantially insoluble, and therefore immobile, in the cosolvent. The insolubility results from formation of the metal-containing polymers; crosslinked polymers which may also be formed are especially insoluble. Because of this immobility and insolubility, the images which are formed will not fade or become blurred with time and can therefore provide precise, accurate, permanent records. The ability to form dark, non-blurring, permanent images is particularly advantageous for recording demographs, such as fingerprints and the like.

One class of useful metal complexing compounds having a plurality of ligand groups are the self-condensed phenolic compounds. Exemplary of these types of compounds are bispyrogallol, bis(gallic acid) tris- and higher pyrogallol and gallic acid compounds as well as the more and less completely hydroxylated analogs such as the self-condensed phenols, catechols, resorcinols, tetrahydroxy benzenes and the like which will complex metals. In addition, the self-condensed esters, ethers, acylates and anhydrides of these phenolic compounds are useful.

A preferred class of metal complexing compounds useful in the present invention are compounds having the formula

wherein R' is a polyvalent organic group having a valence of n, L is a metal-complexing ligand group, and n is a number from 2 to about 100. The particular identity of R' is not critical since its primary function is to couple the ligand groups together and to aid in imparting solubility in oily, liquid cosolvents. Thus, R' should be organophilic and is preferably oleophilic. The more soluble the compound is in the cosolvent, the more readily the compound will react with metal ions to form images.

The ligand groups can be any of the ligand groups which will complex with transition metal ions to form colored products. Hydroxy substituted aromatic groups, and particularly hydroxy substituted benzene rings preferably with at least two hydroxyl groups on the ring and most preferably with the hydroxyl groups in adjacent positions on the ring are preferred. Dithiooxamide and hydroxamino acid derivatives are also preferred ligand groups.

Components of the above formula can be readily prepared by known techniques. For example, the reaction of polyfunctional acids with pyrogallol derivatives can provide bis- and higher pyrogallol derivatives useful in the invention while the gallate esters can be reacted with polyols, such as glycols, to provide the bis- and higher gallate derivatives useful herein. Similarly, the dithiooxamide derivatives can be prepared by methods known in the art as exemplified in U.S. Pat. No. 3,111,423.

A preferred class of metal-complexing compounds containing hydroxy substituted aromatic groups are compounds having the formula

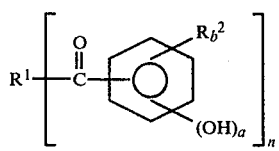

wherein $R^1$ and n are as previously defined; $R^2$ is an organic group independently selected from the group consisting of H or hydrocarbyl, such as alkyl, preferably lower alkyl of 1 to 6 carbon atoms, aryl, aralkyl, cycloalkyl, alkenyl, cycloalkenyl and the like; a is an integer from 1 to 5; b is 0 or is an integer from 1 to 4; and a+b is less than 6.

The identity of $R^2$ is not critical to the invention, however. Care should be taken to choose $R^2$, when present, so that these groups do not prevent the complexing reaction, e.g. by steric effects.

A preferred class of the above compounds results when n is 2 or 3 or mixtures thereof. When n is 2, $R^1$ is a bivalent organic group preferably selected from the group consisting of $-(CR_2^3)_x-$, $-(OCR_2^3CR_2^3O)_x-$,

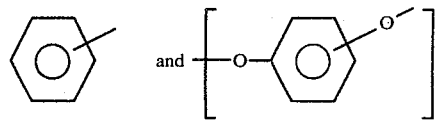

wherein $R^3$ is independently H or hydrocarbyl (as previously defined) and x is 0 or is an integer from 1 to about 100.

Examples of compounds where n=2, i.e. bis-phenolic compounds are the compounds derived from the homologous series of aliphatic difunctional carboxylic acids such as acid, sebacic acid and the like to form the corresponding bis-phenolic compound such as oxaloylpyrogallol, sebacoylpyrogallol. In addition, the polyalkylene glycols, such as polyethylene and polypropylene glycol, can be reacted with gallic acid or the like to provide the corresponding bis-gallate derivative of the glycol.

When n is 3, $R^1$ is a trivalent, organic group preferably selected from the group consisting of —COR-$^3(-CR_2^3-)_2$, —OCR$^3(-CR_2^3O-)_2$,

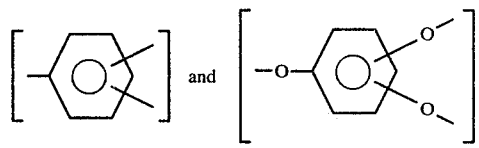

wherein $R^3$ is as previously defined. Thus, phenolic compounds such as pyrogallol reacted with citric acid or gallic acid reacted with glycerine can provide useful metal-complexing compounds.

Where n is greater than 3, $R^1$ is a polyvalent organic group of valence n and can be advantageously selected from the group consisting of

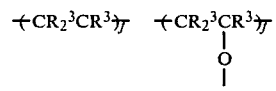

wherein $R^3$ is as previously defined and f is an integer at least 2, up to about 100.

A particularly preferred class of polyvalent organic groups suitable for $R^1$ when n is 2 or 3, or mixtures thereof, is the commercially available dimer and the trimer fatty polycarboxylic acids, and the alcohols derived therefrom, available under the tradename "Empol" from Emery Industries, Inc. Thus, the dimer and trimer acids can be reacted with phenolic compounds such as pyrogallol to obtain metal-complexing compounds having the formula such as

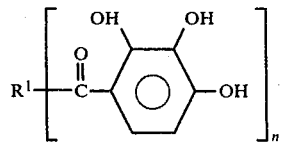

wherein n is 2 or 3 or mixtures thereof; when n is 2, $R^1$ is a hydrocarbon group containing about 34 carbon atoms and when n is 3, $R^1$ is a hydrocarbon group containing about 51 carbon atoms.

Alternatively, when the dimer or trimer alcohol is reacted with gallic acids, compounds are attained having the formula

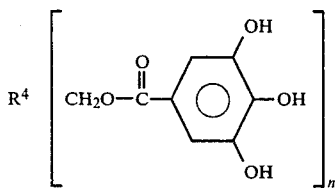

wherein n is 2 or 3 or mixtures thereof; when n is 2, $R^4$ is a hydrocarbon group containing about 34 carbon atoms and when n is 3, $R^4$ is a hydrocarbon group containing about 51 carbon atoms.

Another class of useful metal-complexing compounds are the compounds of the formula $R^1(L)_n$ wherein $R^1$ is a polyvalent organic group having a valence of n and L is a metal complexing ligand group derived from dithiooramide such as a group having the formula

wherein $R^5$ is H or hydrocarbyl. Compounds of this type may be readily prepared in accordance with the teachings of U.S. Pat. No. 3,111,423.

Compounds wherein L is a group having the formula

are also useful to provide dark permanent images when reacted with transition metal salts and particularly provides a black image when reacted with vanadium. These metal-complexing compounds can be prepared by reacting hydroxyl amine with, for example, polyfunctional organic esters.

As indicated above, the color-forming precursor compositions contain metal-complexing compounds having a plurality of ligand groups. The present invention also contemplates mixtures of these compounds with metal-complexing compounds containing a single ligand group. Thus, for metal-complexing compounds containing 2 ligand groups per molecule, up to 50 mole percent of the mono-ligand compound may be included in the composition. When metal-complexing compounds having 3 or more ligand groups are used, proportionately higher mole percents of the mono-ligand material may be used and a dark, permanent image can still be formed.

The color-activating compositions of this invention are compounds which form colored complexes with the aforementioned metal complexing agents, i.e., compounds which provide a color-forming metal ion, preferably a transition metal ion. A particularly preferred class of compounds are the transition metal salts of organic acids. Most preferably, the salts are salts oleophilic, organic acids such as the aliphatic, alicyclic and aromatic carboxylic and sulfonic acids containing at least 6 carbon atoms. Also perfluoroalkylsulfonic acid salts may be used. Exemplary of these compounds are nickel rosinate, nickel 2-ethylhexoate, nickel benzoate, nickel oleate, nickel 2-phenylbutyrate, nickel hydrocinnamate and nickel dinonylnaphthalene sulfonate as well as the corresponding ferrous, ferric cupric and silver analogs of these compounds, and mixtures thereof.

The ferric salts are particularly preferred where a dark, black image is preferred. Ferric benzoate has been found particularly useful in providing intense, black permanent fingerprint records when used with the aforementioned metal complexing compounds.

As noted previously, the metal-complexing reaction is preferably accomplished in the presence of a liquid which is a solvent for the metal complexing compounds as well as the metal ion containing compounds, i.e., a cosolvent. The use of a cosolvent hastens the formation of the colored complex thereby promoting rapid image development. Representative liquid materials which act as cosolvents are hydrocarbon solvents and halogenated hydrocarbon solvents such as 1,1,1-trichloroethane toluene, hexane, xylene and the like, glycols, diesters of organic diacids, mineral oil, low molecular weight oily polymers, phosphates, particularly the alkyl- and polyalkyl phosphates such as tributyl phosphate and trioctyl phosphate, phthalates, polyalkylene glycols such as polypropylene glycol and polyethylene glycol derivatives having the structural formula $R^6O+CH_2CH_2O+_yR^7$ wherein $R^6$ and $R^7$ are hydrogen, lower alkyl containing up to 7 carbon atoms, acyl or aryl and wherein y is at least 2, preferably less than 10 and most preferably 2 to 4. $R^6$ and $R^7$ can be the same or different, and when either $R^6$ and $R^7$ is hydrogen, the complementary $R^6$ or $R^7$ must be alkyl of at least 3 carbon atoms, e.g., $C_3H_7$—, acyl or aryl. The preferred acyl groups are the lower alkanoyl radicals, i.e., $R^8$—CO—, wherein $R^8$ is alkyl containing 1 to 7 carbon atoms. The preferred aryl groups are the substituted or unsubstituted phenyl groups, most preferably the unsubstituted phenyl ($C_6H_5$+ group.

A particularly interesting class of the above cosolvents are tributyl- and trioctylphosphate and mixtures thereof, and the aforementioned polyethylene glycol derivatives, particularly, monophenyl ether of tetraethylene glycol

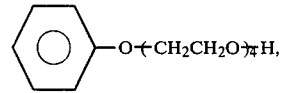

since these compounds when used as cosolvents alone or in admixtures with other cosolvents, exhibit a unique ability to accelerate the complexing reaction and, thus, promote extremely rapid image formation.

In practice, the color-forming precursor composition and the color-activating composition are maintained separate until the color formation is desired. In one embodiment the color-forming precursor composition is coated or transferred onto a receptor sheet. Thus, the coating may be a dry coating on a paper sheet which was deposited from an aqueous slurry and dried. The precursor composition can also be sprayed or coated onto the sheet from a stamp or roller such as a microporous plastic stamp or roller as is commercially available under the tradename "Porelon" available from Porelon, Inc.

Alternatively, the precursor composition can be provided from a transfer sheet containing an encapsulated metal complexing component which will release the metal complexing component under pressure. Thus, the metal-complexing compounds described above can be used with advantage by incorporating the compound in a liquid fill contained in capsules, preferably microcapsules, which can release the fill material by rupture of the capsules. When the metal complexing compounds are to be encapsulated, the compounds should not be so high in molecular weight that the capsule fill solution, which may contain about 5 to 50 percent by weight of the metal complexing compound, exceeds a viscosity of about 1000 centipoise. At higher viscosities encapsulation by known techniques may become difficult. The capsules can be formed by known techniques as described in U.S. Pat. No. 3,516,941 and the aforementioned U.S. Pat. No. 3,682,673. The preferred capsules are microcapsules smaller than about 100 microns and preferably about 5 to 40 microns in size. They may comprise walls of urea formaldehyde, modified urea formaldehyde, gelatin and the like. The coating of the capsules onto a substrate to form a transfer sheet also can be accomplished by known techniques. Generally the capsules are incorporated into an aqueous slurry containing a film-forming binder such as poly vinyl alcohol, polyvinylpyrrolidone or the like. The slurry is coated onto the sheet and dried to form a capsule coating thereon.

A typical liquid capsule fill may comprise 5 to 50% by weight metal-complexing compound and the remainder a liquid carrier such as a hydrocarbon solvent and tributyl phosphate. The ratios of these materials can be varied over a wide range depending on the solubility of the particular metal complexing compound, the solvent volatility desired and the like.

The color-activating composition comprising the transition metal salt may be carried in a separate dispensing means such as an absorbent pad, roller, aerosol dispenser, or other convenient dispensing means. Alternatively, a paper transfer sheet, as noted above, can have a capsule coating containing the metal-containing, color-activating composition.

Typically the color-activating compositions comprise the transition metal salt carried in a liquid which is absorbed in a paper pad, such as a pad of blotter paper, a sponge rubber pad or other pad which will not degrade the composition carried therein. Because the pad may be exposed to the atmosphere for long periods, the liquid carrier is preferably of low volatility. Thus a typical low volatile color-activating composition may contain about 6% by weight ferric benzoate, 15% by weight mono phenyl ether of tetraethylene glycol, 40% by weight tributyl phosphate and 39% by weight trioctyl phosphate.

Typically, the color-activating composition is absorbed in a paper pad to provide about 50% by weight, based on the total weight of the pad and the liquid, of the color-activating composition.

Preferably, the number of transition metal atoms in the combined color-forming composition is about one half the number of ligand groups included in the metal complexing compound to give the darkest, most permanent images. The typical formulations described herein provide compositions in this range. The compositions of this invention have a relatively wide stoichiometric tolerance, and the aforementioned ratios are not critical to the formation of acceptable images.

When one component of the color generating composition is carried in an absorbent pad and the other exists as a coating on a separate sheet, a transfer means may be employed to contact the pad to pick up a small amount of the color-forming component in the pad and transfer it to the desired area of the coated receptor sheet, whereupon the color-generating components become comingled and react to form a visibly colored image on the sheet. The transfer means can be any means capable of transferring the fluid components. Typically the transfer means is an absorbent swab, a rubber stamp, or a portion of a human body, such as a finger or the like.

The present invention has particular utility in providing sensitized sheets, such as personal checks, for receiving the fingerprints of consumers who pay for their purchases by check. Thus, an identification system can be provided, which in combination with a personal check on the like provides means for making fingerprints without inconvenience to the subject.

In the practice of this embodiment of the invention a transfer sheet is provided having a reverse and an obverse surface. The reverse surface contains a coating comprising rupturable microcapsules having a liquid fill which comprises a metal complexing compound and a cosolvent. In addition to the capsule coating, the sheet may have conventional printing on the reverse surface which may be intelligence in mirror image form printed with an ink which is soluble in the cosolvent.

A receptor sheet such as a plain sheet of paper is placed in register underlying the transfer sheet and in contact with the capsule coated surface of the transfer sheet.

By applying pressure to the obverse surface of the transfer sheet, the capsules are ruptured and the liquid fill is transferred to at least a portion of the receptor sheet. In addition the printing on the reverse side of the transfer sheet may be transferred to the receptor sheet by the action of the cosolvent.

The "sensitized" receptor sheet can then be contacted with a finger which has previously contacted a pad containing a color-activating composition. After the finger has contacted the receptor sheet a dark permanent fingerprint will form on the sheet.

The practice of the present invention can be further illustrated by reference to the following examples wherein all percents are expressed as parts by weight unless otherwise indicated.

EXAMPLE 1

A sebacoyl bis-pyrogallol metal-complexing compound was prepared by reacting pyrogallol with sebacic acid by the following general procedure.

Sebacic acid (50.6 g), pyrogallol (126 g), zinc chloride (10.7 g) and 100 ml of xylene were combined in a 500 ml, 3-necked flask fitted with stirrer, thermometer, azeotrope trap, and condenser. The mixture was heated at refluxing pot temperature of about 139° C. for about one hour until the theoretical volume of 9 ml of water was collected in the azeotrope trap.

The pot mixture was poured while hot into a 2 liter flask containing 500 ml water and subjected to steam distillation until essentially a-1 of the xylene was removed. The residue was cooled and collected on a filter. The dull red solid was crystallized from the crystallization solvent (acetic acid water) pair, collected on a filter, washed with water, and allowed to dry in air for about two hours. The crystallized solid's weight was 111.5 grams (theoretical weight is 104.6 grams, so the product was slightly wet) and its melting point (m.p.) was 178°–179° C.

A recrystallization, this time from acetic acid, using decolorizing charcoal gave product of m.p. 182.5°–184° C. Crystallization number 3, from HOAc using charcoal gave m.p. 183°–184° C. Crystallization number 4, using an ethyl acetateheptane solvent pair gave m.p. 183°–184° C.

The compound produced a green-black reaction product when reacted with ferric benzoate.

EXAMPLE 2

An adipoyl bis-pyrogallol metal-complexing compound was prepared by reacting adipic acid (73 g), pyrogallol (126 g) and zinc chloride (21 g) in xylene using the general procedure of Example 1.The compound was crystallized and recrystallized from an ethyl acetate-hexane solvent pair to yield a product having a melting point of 110°–111° C.

The compound produced a green-black reaction product when reacted with ferric benzoate.

EXAMPLE 3

An azeleoyl bis-pyrogallol metal-complexing compound was prepared by reacting azeleic acid (94.1 g), pyrogallol (252 g) and zinc chloride (21 g) in xylene using the general procedure of Example 1. The compound was crystallized and recrystallized from an ethyl acetate-hexane solvent pair to yield a product having a melting point of 179.5°–180.5° C.

The compound produced a green-black reaction product when reacted with ferric benzoate.

EXAMPLE 4

A bis-gallate metal-complexing compound was prepared by reacting methyl-gallate and a dimer glycol by the following procedure.

Methyl gallate (17.5 g), a dimer glycol derived from a dimeric fatty polycarboxylic acid containing about 36 carbon atoms (e.g. "Empol" 1479-83-3-R, Emery Industries, Inc.), and stannous fluoride (0.002 g) were charged into a pyrex test tube 30 cm long and 3.75 in diameter. The test tube was equipped with a nitrogen bubbler, distilling head, condenser, receiver, vacuum guage and water aspirator. The mixture was purged with nitrogen for twenty minutes. The purged mixture in the tube was then heated with a bath liquid of dimethyl orthophthalate at 196° to 240° C. for forty-five minutes at atmospheric pressure giving 0.65 grams distillate.

An additional quantity of 0.002 grams stannous fluoride was added and a vacuum reaching 72.5 cm of mercury was applied. In two hours and 55 minutes the distillate increased to a total of 2.35 grams, most of it in a Dry-Ice cooled trap that had been placed between the receiver and the aspirator.

The brown, tacky product, weighing about 40 grams, was then dissolved in 157.1 grams of tributyl phosphate.

A paper sheet was coated with a mixture of one part of the above solution and eight parts of acetone. When a fingertip was wet with a solution of ferric benzoate in tributylphosphate and monophenylether of tetraethylene glycol and pressed on the coated paper sheet a blue-black print appeared which did not bleed.

EXAMPLE 5

A color-forming precursor composition was prepared having the following composition:

|  | Weight Percent |
| --- | --- |
| *Dimoyl bis-pyrogallol (DBP) | 40.6% |
| Tributyl phosphate | 46.2 |
| Xylene | 11.4 |
| Tridecyl acid phosphate | 0.9 |
| Butylated hydroxytoluene | 0.9 |

*Reaction product of dimeric fatty polycarboxylic acid ("Empol" 1010, Emery Industries, Inc.) and pyrogallol.

The above fill composition was encapsulated in melamine-modified urea formaldehyde capsules having a nominal size of about 35 microns.

The capsules were incorporated into aqueous slurries having a polyvinyl pyrrolidone binder and coated onto paper sheets. The capsule coated surface of the sheet was overprinted with an inked image identifying the finger printing area.

A ferric benzoate color-activating solution was prepared having the following formulation:

|  | Weight Percent |
| --- | --- |
| Ferric benzoate | 6.5% |
| Tributyl phosphate | 39.1 |
| Trioctyl phosphate | 39.1 |
| Monophenylether of tetraethylene glycol ("Pycal" 94, Atlas Chemical Co.) | 15.3 |

The above solution was absorbed in a pad of blotter paper so that the pad contained 50% by weight based on the total weight of the pad and the solution.

Imaging Procedure

A sheet of the dimoyl bis-pyrogallol (DBP) capsule-coated paper (transfer sheet) was nested with a receptor sheet so that the capsule coating was in contact with the receptor sheet. The assembly was then placed onto an aluminum plate in a credit card imprinter so that the area of the receptor sheet on which an image is desired was in register with the aluminum plate. The pressure cylinder of the imprinter was then rolled across the aluminum plate.

Rolling the cylinder across the plate caused breakage of the DBP capsules with subsequent partial transfer of the DBP fill to the receptor sheet. Simultaneously the solvent in the DBP capsules was released and effected partial solvation of the ink used to overprint the design on the DBP capsule-coated surface. The ink was partially transferred to the receptor sheet by the pressure from the roller to provide an image on the receptor sheet.

The receptor sheet bearing a thin coating of DBP and an inked image and the DBP capsule-coated transfer sheet were removed from the imprinter and the transfer sheet discarded. A finger was placed on the pad containing the ferric benzoate and then pressed onto the coated area of the receptor sheet. The DBP and ferric benzoate reacted to form an insoluble, visible image of the fingerprint which did not bleed on long-term storage.

EXAMPLE 6

An experiment similar to that in Example 5 was carried out, except that a metal-complexing compound having a single ligand group, butyroyl pyrogallol, was used in place of the dimoyl bis-pyrogallol. Fingerprints formed from butyroyl pyrogallol and ferric benzoate blurred within 24 hours or less.

What is claimed is:

1. A color-forming precursor composition comprising an organic color-forming, metal-complexing compound having a plurality of ligand groups and an organic cosolvent for said compound, said compound having the formula $$R^1(L)_n$$

wherein
 n is a number from 2 to about 100,
 L is a metal-complexing ligand group, and
 $R^1$ is a polyvalent organic group having a valence of n, provided that when n is 2 or 3 and $R^1$ is a fatty hydrocarbon group, $R^1$ contains about 34 and 51 carbon atoms respectively,
said compound being capable of complexing with transition metal ions to form metal-containing colored products which are substantially insoluble in organic cosolvents for said compound.

2. A composition according to claim 1 wherein L is a metal-complexing ligand group having the formula $$-\overset{O}{\underset{\|}{C}}-NHOH.$$

3. A composition according to claim 1 wherein at least one of said ligand groups comprises a hydroxy-substituted aromatic group.

4. A composition according to claim 1 wherein at least one of said ligand groups comprises a benzene ring having at least two hydroxyl groups substituted on said ring.

5. A composition according to claim 4 wherein at least two of said hydroxyl groups are substituted in adjacent positions on said ring.

6. A composition according to claim 1 wherein said color-forming, metal-complexing compound has the formula $$R^1 \left[ -\overset{O}{\underset{\|}{C}} - \underset{OH}{\overset{OH}{\bigcirc}} - OH \right]_n$$

wherein n is 2 or 3 or mixtures thereof; when n is 2, $R^1$ is a hydrocarbon group containing about 34 carbon atoms, and when n is 3, $R^1$ is a hydrocarbon group containing about 51 carbon atoms.

7. A composition according to claim 6 wherein n is mixtures of 2 and 3 and wherein said composition contains about 3% of the compound wherein n is 3 and about 97% of the compound wherein n is 2.

8. A composition according to claim 1 wherein L is a metal-complexing ligand group derived from dithiooxamide.

9. A composition according to claim 8 wherein said metal-complexing ligand group has the formula $$-NHC\overset{S}{\underset{\|}{C}}\overset{S}{\underset{\|}{C}}NHR^5$$

wherein $R^5$ is H or hydrocarbyl.

10. A composition according to claim 1, wherein said composition includes a reaction accelerating compound selected from the group consisting of tributyl phosphate and a compound having the formula $R^6O+CH_2CH_2O+_yR^7$, and mixtures thereof, wherein $R^6$ and $R^7$ are hydrogen, lower alkyl acyl or aryl and wherein y is 2–10 and when either of $R^6$ or $R^7$ is hydrogen, the complementary $R^6$ or $R^7$ is lower alkyl of at least 3 carbon atoms, acyl or aryl.

11. An encapsulated, color-generating precursor composition comprising rupturable microcapsules containing a liquid fill comprising the precursor composition of claim 1.

12. A composition for providing a dark, permanent image on substrates comprising a color-forming precursor composition and a color-activating composition, said precursor composition comprising the composition of claim 1 and said color-activating composition comprising a transition metal salt of an oleophilic, organic salt.

13. A composition according to claim 12, wherein said transition metal salt is ferric benzoate.

14. A composition according to claim 12, wherein the number of moles of transition metal salt is about one-half the number of ligand groups included in said metal-complexing compound.

15. A sheet-like substrate having at least a portion of one major surface coated with the color-forming precursor composition of claim 1.

16. A method of providing a dark, permanent image on a sheet-like substrate comprising
 (a) coating at least a portion of one major surface of said substrate with the color-forming precursor composition of claim 1; and
 (b) contacting a color-activating composition with a transfer means and subsequently contacting said substrate surface with said transfer means whereby said color-activating composition is brought into contact with said color-forming precursor composition and a dark, permanent image is formed on said substrate.

17. A method according to claim 16, wherein said transfer means is a portion of a human body.

18. A method of providing a dark, permanent image on paper comprising
 (a) providing a transfer sheet having at least a portion of one major surface coated with rupturable microcapsules containing a liquid fill, said liquid fill comprising a color-forming precursor composition according to claim 1;
 (b) juxtaposing said transfer sheet overlying a receptor sheet such that the capsule coated surface of the transfer sheet is in contact with the receptor sheet;
 (c) applying pressure to the obverse surface of said transfer sheet to rupture at least a portion of said microcapsules and transfer at least a portion of said color-forming precursor composition to at least a portion of said receptor sheet thereby sensitizing portions of said receptor sheet;
 (d) separating said receptor sheet and said transfer sheet; and (e) contacting a color-activating composition with a transfer means and subsequently contacting a sensitized area of said receptor sheet with said transfer means whereby said color-activating composition is brought into contact with said color-forming precursor composition to form a dark, permanent image in said sensitized area of said receptor sheet.

19. A method according to claim 18 wherein said transfer means is a portion of a human body.

20. A method according to claim 18 wherein said transfer sheet has images in mirror-image form on said capsule coated surface, said images comprising visible ink which is at least partially soluble in said cosolvent and is transferred to said receptor sheet when said capsules are ruptured.

21. A composition according to claim 1 wherein n is 3 or mixtures of 2 and 3.

22. A method of making dark, permanent, non-migrating images in a cosolvent environment on a paper substrate comprising (a) coating at least a portion of the substrate with the color-forming precursor composition of claim 1 and wherein said cosolvent includes a reaction accelerating compound selected from the group consisting of trioctyl phosphate, tributyl phosphate and a compound having the formula $R^6O + CH_2CH_2O +_y R^7$, and mixtures thereof, wherein $R^6$ and $R^7$ are hydrogen, lower alkyl, acyl or aryl and wherein Y is 2–10 and when either of $R^6$ or $R^7$ is hydrogen, the complementary $R^6$ or $R^7$ is lower alkyl of at least 3 carbon atoms, acyl or aryl, and (b) contacting a color-activating composition with a transfer means and subsequently contacting said substrate surface with said transfer means whereby said color-activating composition is brought into contact with said color-forming precursor composition and a dark, permanent, non-migrating image is formed.

23. A composition according to claim 1 wherein said color-forming, metal-complexing compound has the formula

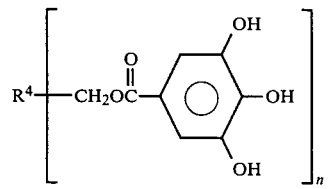

wherein
n is 2 or 3 or mixtures thereof;
when n is 2, $R^4$ is a hydrocarbon group containing about 34 carbon atoms, and
when n is 3, $R^4$ is a hydrocarbon group containing about 51 carbon atoms.

24. A color-forming precursor composition according to claim 1 wherein said composition contains a sufficient amount of said compound wherein n is 3 or greater to provide crosslinked complexes with transition metal ions which are substantially insoluble in organic cosolvents for said compounds.

25. A color-forming precursor composition comprising an organic color-forming, metal-complexing compound having a plurality of ligand groups and an organic cosolvent for said compound, said compound having the formula

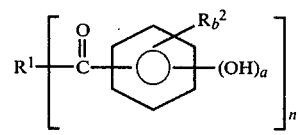

wherein
n is a number from 2 to about 100
$R^1$ is a polyvalent organic group having a valence of n
$R^2$ is an organic group independently selected from the group consisting of H, or hydrocarbyl,
a is an integer from 1 to 5, and
b is o or an integer from 1–4 and a+b is less than 6.

26. A composition according to claim 25 wherein a is at least 2 and at least 2 of said hydroxyl groups are in adjacent positions.

27. A composition according to claim 25 wherein $R^2$, a and b are as previously defined;
n is 2; and
$R^1$ is a bivalent, organic group selected from the group consisting of

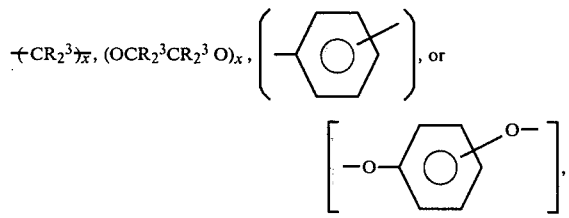

wherein
$R^2$ is independently H or hydrocarbyl; and
X is 0 or is an integer up to about 100.

28. A composition according to claim 25 wherein $R^2$, a and b are as previously defined;
n is 3; and
$R^1$ is a trivalent, organic group selected from the group consisting of $-COR^3 + CR_2^3 +_2$, $-OCR^3 + CR_2^3 O +_2$,

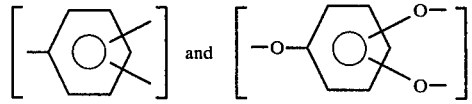

wherein
$R^3$ is as previously defined.

* * * * *